United States Patent
Batke et al.

(10) Patent No.: US 7,291,155 B2
(45) Date of Patent: Nov. 6, 2007

(54) SYSTEM WITH A SURGICAL NEEDLE AND A HANDLE

(75) Inventors: Boris Batke, Lubeck (DE); Raimo Sump, Hamburg (DE)

(73) Assignee: Ethicon, GmbH, Norderstedt (DE)

( * ) Notice: Subject to any disclaimer, the term of this patent is extended or adjusted under 35 U.S.C. 154(b) by 537 days.

(21) Appl. No.: 10/399,791

(22) PCT Filed: Mar. 6, 2002

(86) PCT No.: PCT/EP02/06048

§ 371 (c)(1),
(2), (4) Date: Sep. 25, 2003

(87) PCT Pub. No.: WO03/017848

PCT Pub. Date: Mar. 6, 2003

(65) Prior Publication Data

US 2004/0116962 A1    Jun. 17, 2004

(30) Foreign Application Priority Data

Aug. 23, 2001   (DE) ............................... 101 41 234

(51) Int. Cl.
*A61B 17/42* (2006.01)
(52) U.S. Cl. ...................................... 606/119; 606/148
(58) Field of Classification Search .................. 606/99, 606/119, 145, 148; 600/30, 567, 36
See application file for complete search history.

(56) References Cited

U.S. PATENT DOCUMENTS

| | | | |
|---|---|---|---|
| 5,474,543 A | 12/1995 | McKay | |
| 5,603,718 A * | 2/1997 | Xu | 606/145 |
| 6,030,393 A | 2/2000 | Corlew | |
| 6,258,107 B1 * | 7/2001 | Balazs et al. | 606/153 |
| 6,468,279 B1 * | 10/2002 | Reo | 606/79 |
| 6,554,778 B1 * | 4/2003 | Fleming, III | 600/567 |
| 6,612,977 B2 * | 9/2003 | Staskin et al. | 600/30 |

FOREIGN PATENT DOCUMENTS

| | | |
|---|---|---|
| EP | 1093758 A1 | 4/2001 |
| WO | WO 9606567 A1 | 3/1996 |

OTHER PUBLICATIONS

PCT Search Report for PCT/EP 02/06048 dated Sep. 26, 2002.

* cited by examiner

*Primary Examiner*—Tan-Uyen Ho
*Assistant Examiner*—Natalie Pous

(57) ABSTRACT

In a system with a surgical needle and a handle, the surgical needle has in its proximal end-section, lying opposite the needle tip, a holding section (14), which is set up for insertion into the handle. The handle has a channel (32), set up for holding the holding section (14) of the surgical needle, and a locking device (50, 70) with a locking element (50) which is displaceable in longitudinal direction of the channel (32) from a locking position, in which the holding section (14) is fixed to the handle, into a release position, in which the holding section (14) can be pulled out from the channel (32).

1 Claim, 3 Drawing Sheets

SYSTEM WITH A SURGICAL NEEDLE AND A HANDLE

Figure 1:
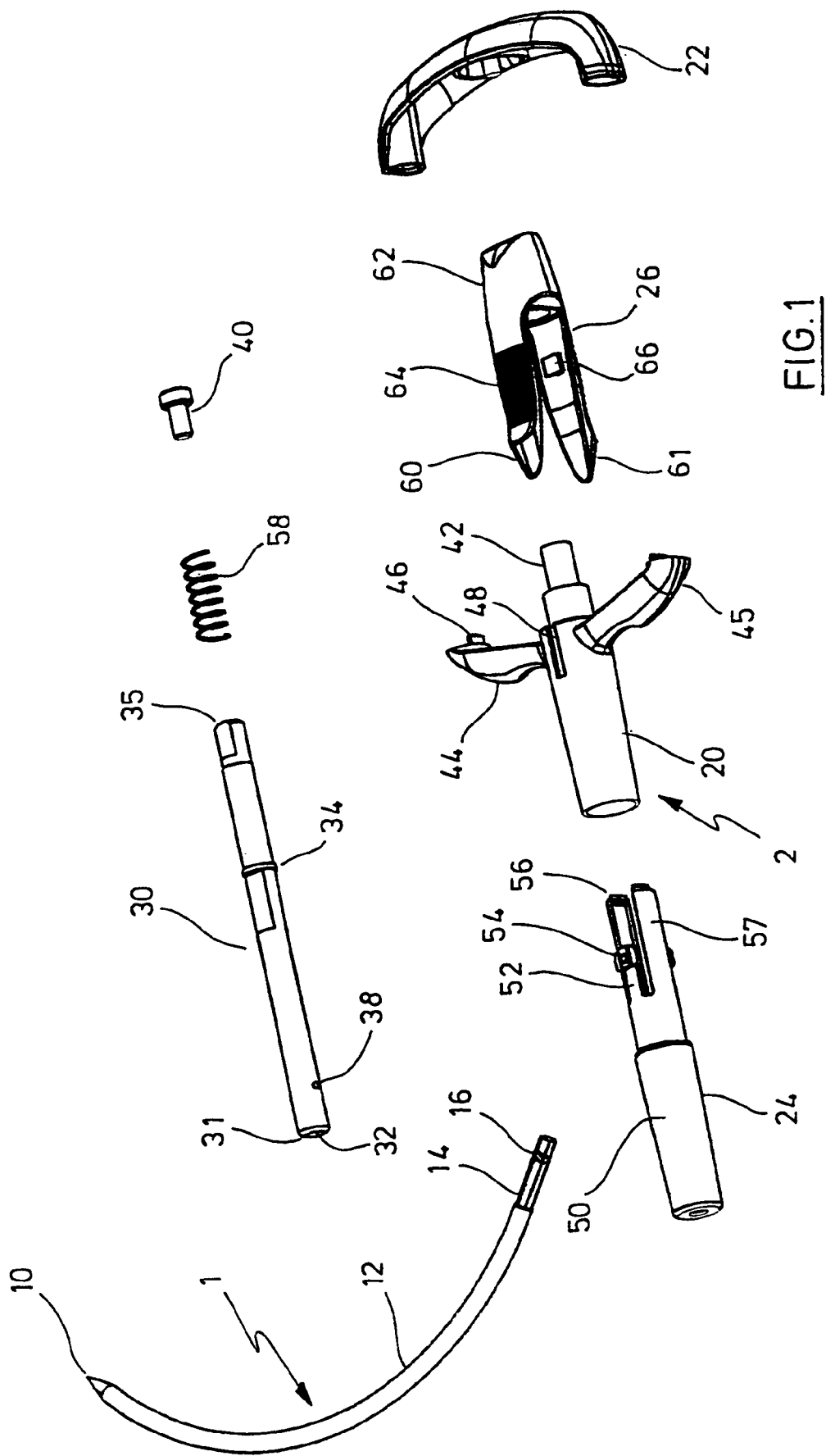

The invention relates to a system with a surgical needle and a handle.

There are surgical techniques in which thick to very thick surgical needles are used, e.g. needles with a diameter of 2 mm to 7 mm. Such needles are used for example in order to insert a tape underneath the urethra of a patient for the treatment of stress incontinence.

Such a large needle can often be handled by the operator only with difficulty. If the needle is guided through tissue, considerable forces arise. The operator can admittedly use a needle holder or a forceps-like surgical instrument when handling the needle. However, as a rule, he often has to reattach this instrument to the needle, which is awkward. Furthermore, unfavourable leverage conditions can occur, in particular if the instrument runs at an angle to the needle.

In the case of a previously known system with a surgical needle and a handle, the handle to which the proximal end-region of the needle lying opposite the tip of the needle is attached facilitates handling. A screw screwed into the proximal face of the needle serves to secure it. In order to pull the needle completely through the body tissue of the patient, the needle has to be detached from the handle. This is awkward, however, because to do this the screw has to be unscrewed first.

It is the object of the invention to provide a possibility of facilitating the handling of a surgical needle, in particular a thick surgical needle.

This object is achieved by a system with a surgical needle and a handle with the features of claim 1. Advantageous versions of the invention emerge from the dependent claims. Claim 15 relates to a surgical needle and claim 16 to a handle which are set up for such a system.

The system according to the invention contains a surgical needle and a handle. In its proximal end-region lying opposite the needle tip, the surgical needle has a holding section which is set up for insertion into the handle. The handle has a channel set up for holding the holding section of the surgical needle and a locking device. The locking device has a locking element which is displaceable in longitudinal direction of the channel from a locking position in which the holding section is attached to the handle, into a release position in which the holding section can be pulled out from the channel.

If the holding section is locked at or fixed to the handle, the surgical needle is firmly and securely connected to the handle. In this position, the handle substantially facilitates the handling of the needle. Thus, e.g., the needle can be held and guided with the help of the handle if it is moved towards the tissue of a patient, placed in position there and pushed through. The suture material, the tape or a similar object which is to be pulled through the tissue with the help of the needle, can be attached to the shaft of the surgical needle between the holding section and the needle tip, preferably near the holding section, e.g. with the help of a shrink-on tube. For this purpose the surgical needle preferably has, distal to the holding section, an attachment section for a suture material, tape or similar, e.g. a section of the shaft, provided with grooves, which can also be provided with a step, against which e.g. the shrink-on tube lies, in order to facilitate a continuous transition between the shaft and the suture material, tape or similar.

If the surgical needle has penetrated the body roughly up to the shoulder of the handle, the needle tip has already left the tissue at the desired point where it or the section of the shaft following the needle tip can be gripped manually by the operator (or with a customary instrument). At this time, the locking element can be moved quickly and in a user-friendly manner from the locking position into the release position, so that the needle can be pulled out of the handle without jerking and expending little force (or conversely the handle can be pulled off the needle). The needle can be pulled fully through the tissue, after the release of the handle, with the suture material, tape or similar attached to the needle.

The surgical needle can have a diameter of 2 mm to 7 mm, however another diameter is also conceivable.

The holding section of the surgical needle preferably deviates from a circular form at least in part of its cross-section, and the channel of the handle is matched in its cross-section to the holding section to secure the surgical needle against twisting. This design makes it possible in an easy way to connect the needle to the handle, secured against rotation.

The channel preferably extends from an opening in the distal end area of the handle, and the holding section of the surgical needle is set up for longitudinal insertion into this opening.

In a preferred version of the invention, the holding section of the surgical needle has at least one recess, in which in the locking position at least one blocking element provided on the locking device of the handle engages. The blocking element is mounted moveable transversely to the longitudinal direction of the channel, the locking element blocking a movement of the blocking element when in the locking position, but freeing it when in the release position. The blocking element preferably includes a ball which projects, when in the locking position, into the internal space of the channel and, when the needle is inserted, engages in the recess at the holding section of the needle. The channel is preferably formed in a metal sleeve, the ball guided in a recess in the wall of the metal sleeve, and the diameter of the ball is greater than the thickness of the wall in the area of the recess. The locking element can have a sleeve which can be displaced in longitudinal direction of the metal sleeve and which surrounds the metal sleeve, which sleeve has a conical inner surface in the area of the ball and engages against the ball when in the locking position and permits a radial shift of the ball when in the release position.

This preferred design of the invention allows for a convenient and secure handling of the surgical needle. When needed, the locking element can be conveniently and quickly pushed into the release position with the help of an activating element provided on the handle, so that the surgical needle can be released from the handle with slight exertion of force. A further advantage of this version is that plastic can be used as basic material for the handle; through the use of the metal sleeve (which can be cheaply produced) the highly-stressed channel area acquires a stability which is sufficient to secure the holding section of the surgical needle.

Preferably, a spring biases the locking element into the locking position. This guarantees that, in normal position, the surgical needle is locked at the handle. In addition, a safety device can be provided on the handle which is set up to secure the locking element against an unintentional movement into the release position (which could occur even against the spring force). In order to activate the safety device, an ergonomically designed activating element is preferably provided which can be coupled with the activating element for displacing the locking element.

The handle is preferably made substantially from plastic and can be designed as a disposable article. It preferably has a multi-part housing, so that the locking device can be fitted without any problems.

In a preferred version of the invention, the handle has at least one widening structure in the area of its proximal end, which allows the handle to rest comfortably in the palm of the hand or against the ball of the hand of the operator. The handle can additionally have at least one finger-rest structure, e.g. two wing-like structures extending on opposite sides, which run parallel to the widening structure and with the help of which the operator can e.g. pull the handle onto the palm of his hand with the index finger and the middle finger, so that it rests securely in his hand. A further advantage of this version can be observed when the needle is bent. The operator can then deduce from the position of the widening structure or the finger-rest structure the direction in which the front (distal) section of the needle is running.

Figure 2:
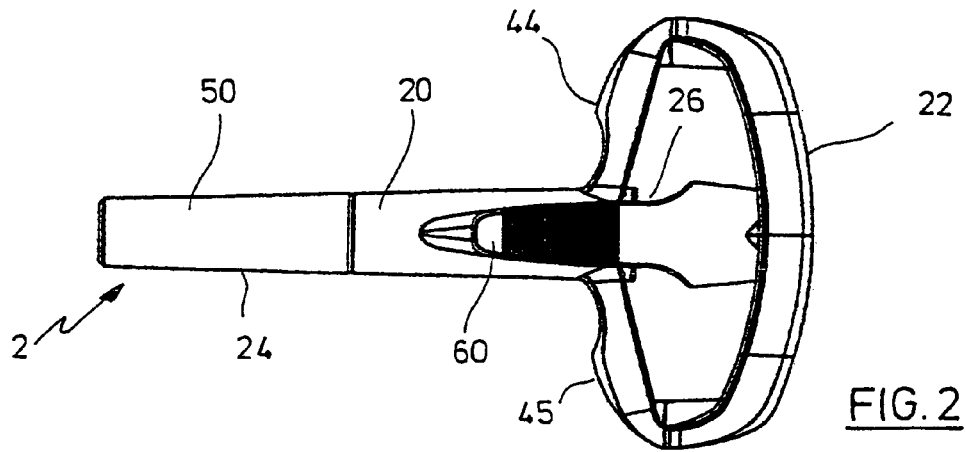
Figure 3:
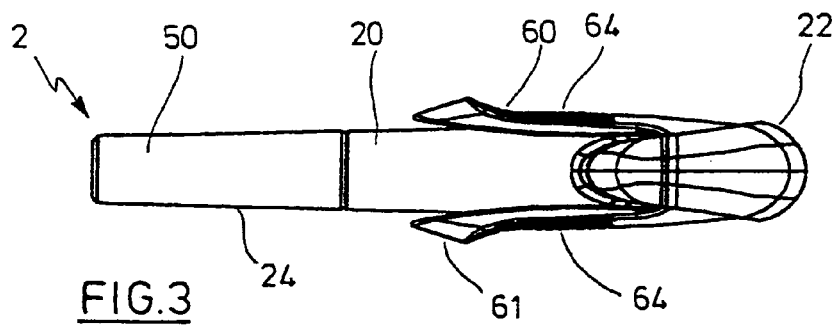
Figure 4:
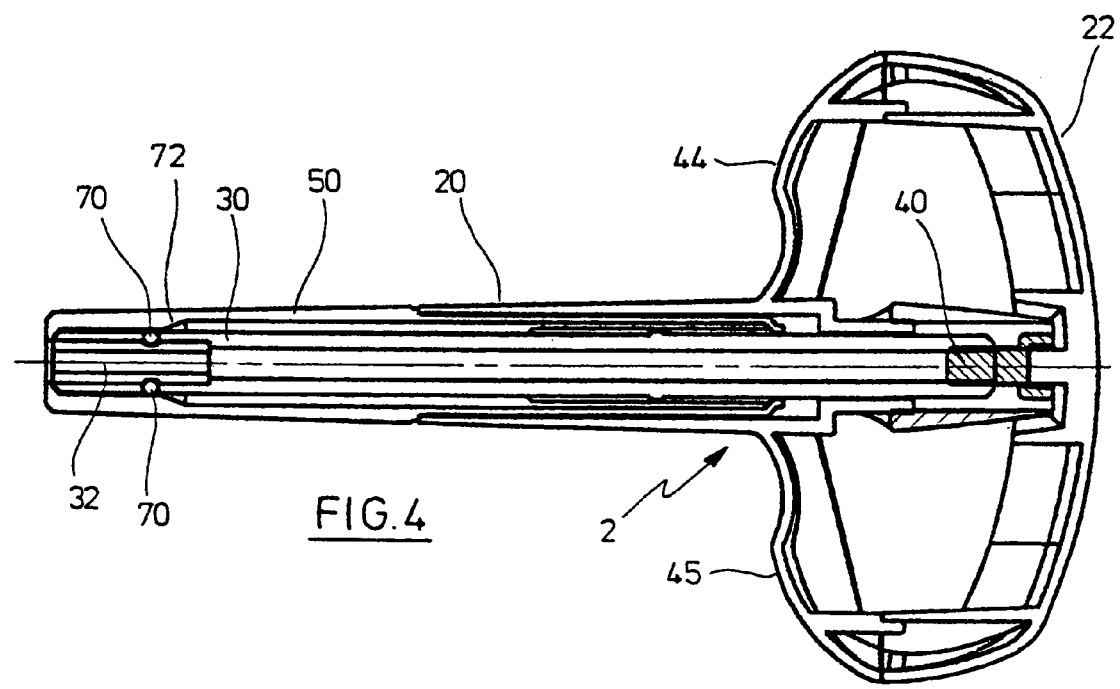

The invention is explained in more detail in the following, using an embodiment. The drawings show in FIG. 1 an exploded view of a version of the system according to the invention, FIG. 2 a top view of the handle of the version from FIG. 1 when fitted, FIG. 3 a side view of the handle of the version from FIG. 1 when fitted, FIG. 4 a longitudinal section through a slightly modified version of the handle when fitted, FIG. 5 a longitudinal section through the distal area of the handle with the surgical needle inserted, which illustrates the locking position, and FIG. 6 a longitudinal section through the distal area of the handle with the surgical needle inserted, which illustrates the release position.

FIG. 1 is an exploded view of a version of a system with a surgical needle 1 and a handle 2 and shows the individual parts of the embodiment.

The surgical needle 1, which forms a component of the system, has a needle tip 10 at its distal end. Connected to this is a shaft 12 which is bent in the embodiment and has a maximum diameter of 5 mm. In its proximal end-section the needle 1 has a holding section 14, which is designed with a hexagonal cross-section. A groove-like recess 16 extends over the circumference of the holding section 14 (see also FIG. 5 and FIG. 6).

Represented in the lower part of FIG. 1 are four parts of the handle 2 which, in the embodiment, are each made in one piece from plastic, namely a housing part 20, a handle end-piece 22, a locking element 24 and an activating element 26. How these parts as well as a metal sleeve 30, which is shown in the upper part of FIG. 1, are assembled, can be best seen from an over-all view of FIGS. 1 to 4. In short, the metal sleeve 30 is located in the housing part 20 and is, like the handle end-piece 22, firmly connected to it; the locking element 24 and the activating element 26 are locked together and can be displaced in longitudinal direction of the handle 1 relative to the other parts.

The metal sleeve 30 consists of stainless steel, in the embodiment. Extending in longitudinal direction from its open distal end 31 is a channel 32 which has a hexagonal cross-section in its distal section and can accommodate the holding section 14 of the needle 1 completely and securely against rotation. The metal sleeve 30 contains a projecting collar 34 in its central area and an internal thread for accommodating a screw in the area of its proximal end 35. In the proximity of the distal end 31, the wall 36 of the metal sleeve 30 is provided with two recesses 38, see also FIG. 6. The cross-section of the holding section 14 and the cross-section of the channel 32 matched to this, deviate from the shape of an equilateral hexagon, so that the needle 1 can be inserted into the channel 32 only in an unequivocal way.

With the help of a screw 40 which is screwed into the internal thread at the proximal end 35 of the metal sleeve 30, the metal sleeve 30 is attached to the proximal end-section 42 of the housing part 20. The metal sleeve 30 is secured against rotation by a flattened area near its proximal end 35.

The housing part 20 contains two finger-rest structures 44 and 45, at the end of each of which a locking projection 46 is located. The locking projections 46 project into corresponding recesses on the handle end-piece 22, in order to connect the handle end-piece 22 firmly to the housing part 20. Furthermore, the wall of the housing part 20 is provided with a slit 48 and an identical slit lying diametrally opposite this.

The locking element 24, which is designed in one piece in the embodiment, but which in principle can also consist of several parts, has in its distal section a sleeve 50 which, when fitted, surrounds the metal sleeve 30. Two spring tongues 52 extend from the sleeve 50, which are each provided with a locking projection 54 at their ends, and two guiding parts 56 and 57, which are somewhat longer than the spring tongues 52. When the handle 2 is fitted, the locking projections 54 project through the slits 48.

Figure 5:
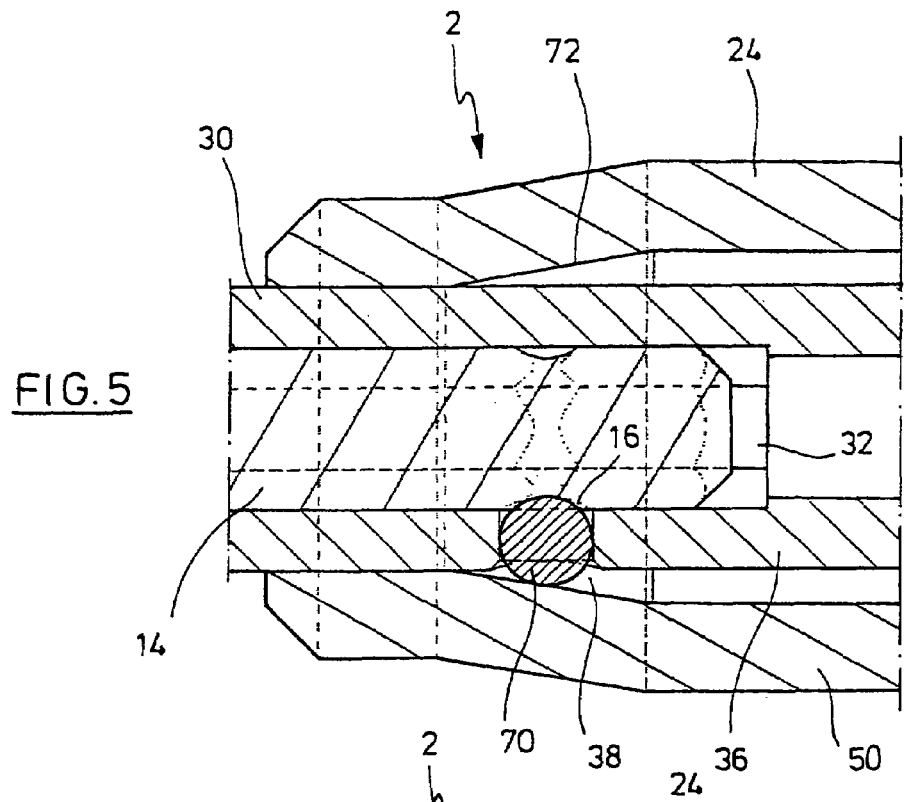

A compression spring 58, which is guided by the metal sleeve 30 and rests against it (not shown in FIG. 4), presses against the locking element 24, so that the locking element 24 is so pre-stressed that in the "normal state" (i.e. without exposure to external force) it is displaced in proximal direction relative to the metal sleeve 30 (locking position, see FIG. 5).

The activating element 26 contains two side parts 60 and 61, which extend from an end piece 62 and are provided with gripping grooves 64 on their outsides. A locking recess 66 is located on the insides of each of the side parts 60 and 61. When fitted, the locking recesses 66 are locked with the locking projections 54 projecting through the slits 48. The activating element 26 and the locking element 24 are thereby connected to each other. In order to displace the locking element 24 with the help of the activating element 26 relative to the housing part 20 and the metal sleeve 30 and against the force of the compression spring 58, the two side parts 60 and 61 of the activating element 26 must be pressed against each other in order to release a catch arranged on the locking projections 54 and the slits 48 (not shown in detail in the figures). This serves as safety device, so that the locking element 24 cannot be displaced by mistake. The design of the activating element 26 with the two side parts 60 and 61 and the gripping grooves 64 is ergonomic and allows a problem-free operation with surgical gloves.

Figure 6:
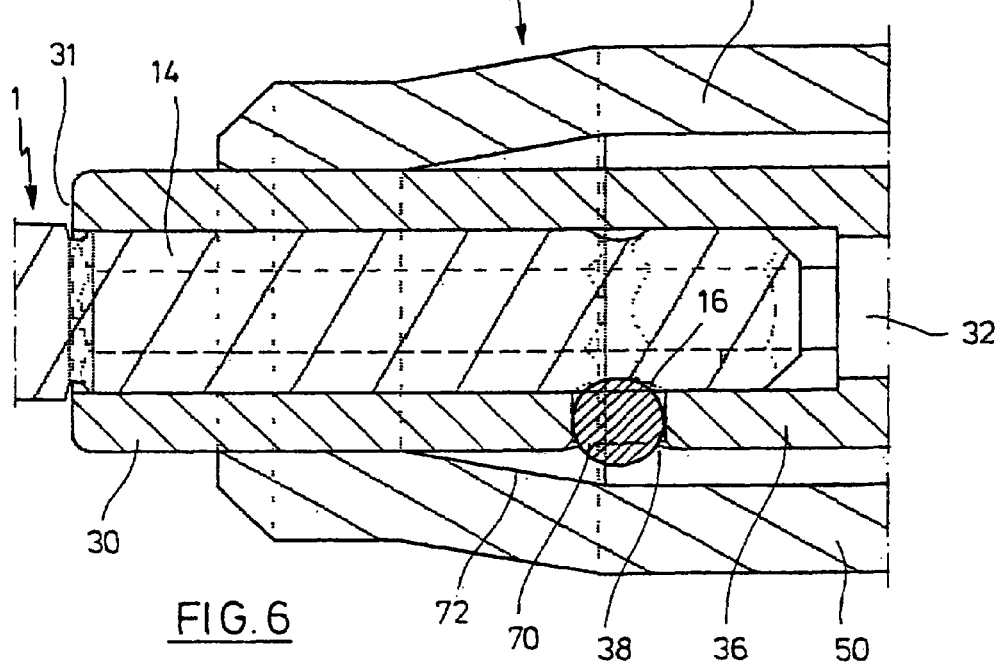

The mode of operation of the locking device is obvious from FIGS. 5 and 6; it enables the surgical needle 1 to be either connected firmly and securely to the handle 2 or else released, so that it can be pulled out of the channel 32 without any problems.

FIG. 5 shows the locking position in which the holding section 14 is secured to the handle 2. A ball 70 is guided in each of the recesses 38, which extend in the area of the channel 32 and the holding section 14 through the wall 36 of the metal sleeve 30. As the recesses 38 are designed in a slightly conical manner, the balls 70 cannot fall inwards into the channel 32. A radial movement outwards is possible, on the other hand, the sleeve 50 preventing the ball in question 70 from emerging fully from the recess 38. In the area of the balls 70, the sleeve 50 has a conical inner surface 72. In the locking position, the conical inner surface 72 lies against the balls 70, while the balls 70 engage in the recess 16 on the holding section 14 of the needle 1. As the balls 70 cannot escape outwards in this position, the needle 1 cannot be pulled out of the channel 32. In this position, it is thus securely and firmly connected to the handle 2.

If the two side parts 60 and 61 of the activating element 26 are pressed against each other and the explained safety device is thereby released, the locking element 24 with the sleeve 50 can be displaced relative to the metal sleeve 30, that is to the left in the representation according to FIGS. 5 and 6. When the release position shown in FIG. 6 is reached, the balls 70 are no longer prevented from moving outwards radially. The needle 1 can therefore be pulled out of the channel 32, the groove-like recess 16 pressing the balls 70 radially outwards.

The invention claimed is:

1. A system with a surgical needle and a handle, wherein the surgical needle further comprises a distal end terminating in a needle tip and a proximal end having a holding section sized and shaped for insertion into the handle, and wherein the handle has a channel therein extending along a longitudinal axis, the channel being sized and shaped for receiving therein the holding section of the surgical needle, and further comprises a locking device with a locking element, the locking element being movable from a locking position at a first distance along said longitudinal axis to a release position at a second distance along said longitudinal axis, wherein in the locking position the holding section is fixedly secured within the channel, and in the release position the holding section can be removed from the channel, wherein at least a portion of the cross-section of the holding section of the surgical needle deviates from a circular cross-section, and wherein the channel of the handle has a complementary cross-section so as to secure the surgical needle therein against twisting, wherein the holding section of the surgical needle has at least one recess therein, and wherein the locking device further comprises at least one blocking element that engages the at least one recess in the locking position, wherein the blocking element is movable in a direction substantially transverse to the longitudinal axis of the channel, and wherein the locking element prevents movement of the blocking element when in the locking position, and wherein the blocking element includes a ball that projects, when in the locking position into the channel and, when the needle is inserted in the channel, engages in the at least one recess therein, wherein the channel is formed in a metal sleeve having a recess therein for receiving the ball, and wherein the diameter of the ball is greater than a thickness of sleeve wall, and wherein the locking element has a sleeve displaceable in a longitudinal direction of the metal sleeve and surrounding the metal sleeve, and wherein the locking element sleeve has a substantially conical inner surface in the area of the ball that engages the ball when in the locking position, and permits radial movement of the ball when in the release position.

* * * * *